United States Patent
Barkhoudarian

(10) Patent No.: US 7,392,713 B2
(45) Date of Patent: Jul. 1, 2008

(54) MONITORING SYSTEM FOR TURBOMACHINERY

(75) Inventor: Sarkis Barkhoudarian, West Hills, CA (US)

(73) Assignee: United Technologies Corporation, Hartford, CT (US)

(*) Notice: Subject to any disclaimer, the term of this patent is extended or adjusted under 35 U.S.C. 154(b) by 1162 days.

(21) Appl. No.: 10/260,315

(22) Filed: Sep. 30, 2002

(65) Prior Publication Data

US 2004/0060371 A1    Apr. 1, 2004

(51) Int. Cl.
*F01D 17/00* (2006.01)

(52) U.S. Cl. ............... 73/862.331; 415/10; 415/17; 324/160; 324/174; 324/207.13; 73/660

(58) Field of Classification Search ............ 700/275; 324/160, 164, 207.12, 207.13, 225, 239, 324/174, 173; 73/862.331, 660; 60/660; 415/10, 47, 108, 173.1, 17
See application file for complete search history.

(56) References Cited

U.S. PATENT DOCUMENTS

| | | | |
|---|---|---|---|
| 4,502,832 A | | 3/1985 | Becker |
| 4,741,203 A | | 5/1988 | Willaman et al. |
| 4,804,905 A | * | 2/1989 | Ding et al. ............... 324/662 |
| 4,884,071 A | | 11/1989 | Howard |
| 4,967,153 A | * | 10/1990 | Langley ............... 324/174 |
| 4,972,332 A | | 11/1990 | Luebbering et al. |
| 5,169,242 A | | 12/1992 | Blasé et al. |
| 5,304,926 A | | 4/1994 | Wu |
| 5,312,225 A | | 5/1994 | Lorenzen |
| 5,459,674 A | | 10/1995 | Ide et al. |
| 5,552,711 A | | 9/1996 | Deegan et al. |
| 5,942,893 A | * | 8/1999 | Terpay ............... 324/164 |
| 6,247,900 B1 | | 6/2001 | Archibald et al. |

OTHER PUBLICATIONS

Isotech, Inc., Precision Linear Motion Products, Metal Sensors, http://www.isotechinc.com/prod15.htm.

* cited by examiner

*Primary Examiner*—Leo Picard
*Assistant Examiner*—Charles Kasenge

(57) ABSTRACT

A sensing system for monitoring a property of an electrically conductive moving element of turbomachinery. The sensing system includes a sensing system housing. A magnetic core is contained within the sensing system housing. A coil is positioned about at least a portion of the core. The coil is electrically connectable to a property data analysis device. A first magnet and a second magnet are positioned about the coil and positionable proximate a moving element of turbomachinery to be monitored. A primary magnetic field is generated by the first and second magnets. When the moving element enters the primary magnetic field a current is induced in the moving element, thus generating a time-variable magnetic field and commensurate voltage signal generated in the coil. The voltage signal is amplified by the magnetic core and provides an indication of a property of the moving element.

44 Claims, 5 Drawing Sheets

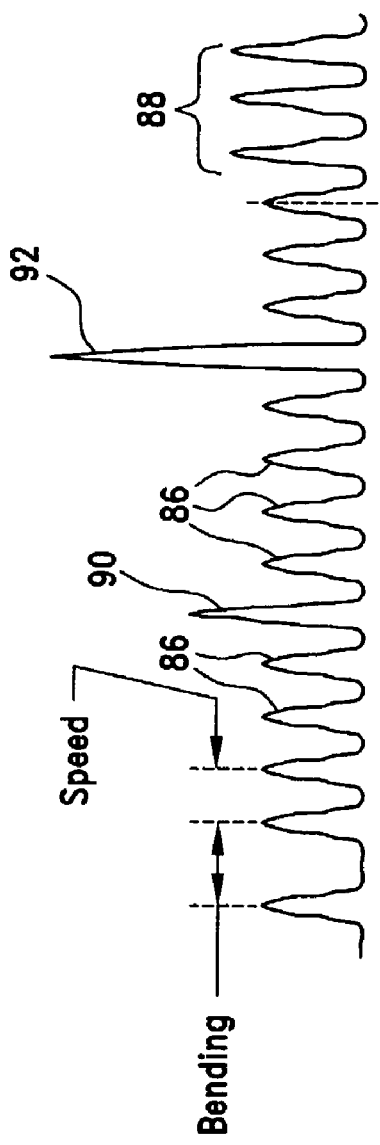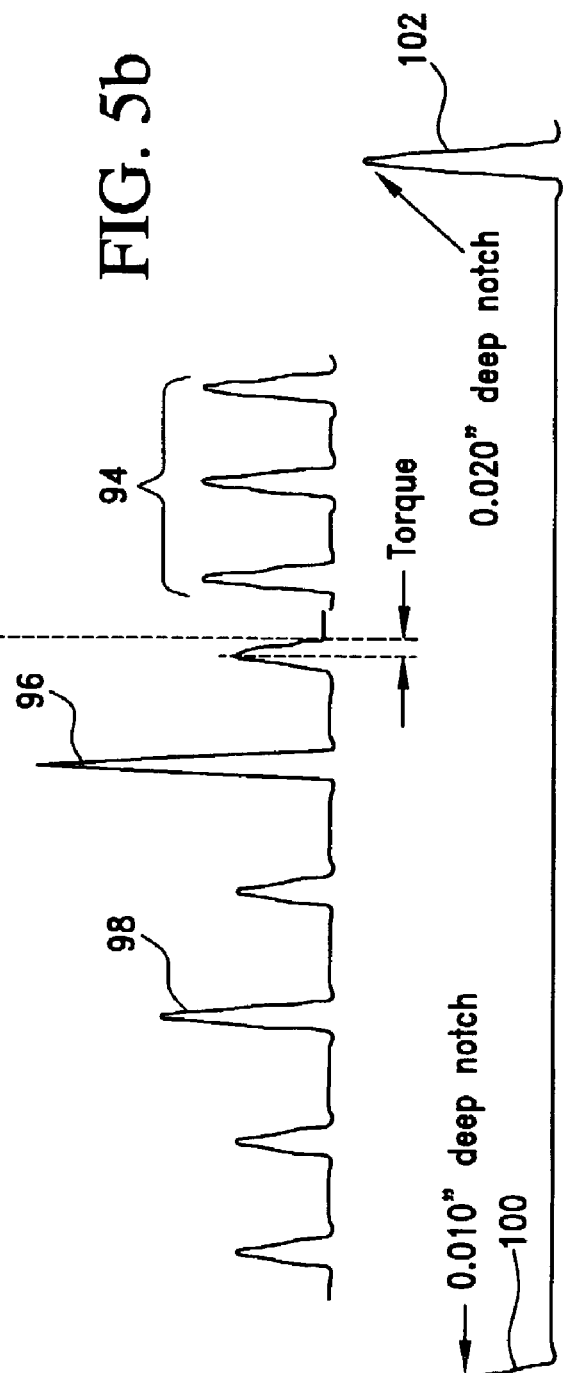

MONITORING SYSTEM FOR TURBOMACHINERY

BACKGROUND OF THE INVENTION

1. Field of the Invention

The present invention relates to the monitoring and control of turbomachinery and more particularly to an electromagnetic, non-intrusive sensing system.

2. Description of the Related Art

Currently, within the fields of jet engines, rocket engines and rotary engines, blade/impeller/gear elongation, bending, twisting, shaft travel, runout, torque, horsepower and disc precession are generally not measured in real time. Thus no real-time data is provided to detect the blade/impeller/disc degradation and imminence of blade/impeller/shaft rubbing, which can cause shearing of housings, explosions in flammable fluids or instability of the disc/shaft that can cause catastrophic disc/shaft fracture. Currently, turbines are redlined for safety, based on a single-point real-time gas temperature measurement, not the blade thermal or fatigue survivability limit. Since the exact blade temperature cannot be derived from gas temperature, the threshold temp is usually set at a lower value for safety and blade life reasons, thus reducing the turbomachinery potential efficiency and power output. Current pump designs allow a large impeller gap to prevent hazardous impeller rubbing, causing pump inefficiency. In addition, accelerometers are used to presumably detect some of these failures. However, accelerometers have not been able to detect all these failures consistently, and even occasionally have resulted in false alarms.

Currently, to prevent the above-mentioned failures, scheduled manual intrusive inspections are performed, using borescope, shaft travel gages, filler gages, radiographic films, dye penetrants, eddy current inspection, etc., that require laborious disassembly and subjective interpretation.

To prevent blade damage, the turbines have been redlined at lower temperatures, sacrificing valuable thermodynamic efficiency or maximum power. Similarly, the pumps have been designed with larger gaps to prevent catastrophic impeller rubbing, again sacrificing efficiency.

Isotech, Inc., of Horsham, Pa., markets a Metal Motion Sensor/Encoder that has the ability to sense metals in motion in such cases as gear speed applications through a non-magnetic stainless steel wall. However, the Isotech device requires electrical excitation which is undesirable in aerospace propulsion systems because it may potentially result in a catastrophic explosion. Such an explosion may result if the wire leads therein become exposed to internal turbine gases. Furthermore, this sensor has a very low frequency response.

U.S. Pat. No. 4,741,203, issued to D. O. Willaman et al., discloses an inspection device which permits inspection of the interior of a turbine for metal integrity. The inspection device is mounted on a sensor assembly that engages a turbine blade and rests on the turbine disc. Metal integrity sensors are mounted on the sensor assembly and inspect various areas of turbine blades and turbine rotor steeples. The associated coil assembly provides a coil of wire and magnetic shielding which improves the sensitivity of the metal integrity sensors. The associated method provides for proper positioning of the apparatus and inspecting the turbine for metal integrity. This device is positioned within the interior of the turbo machinery and is therefore intrusive and undesirable.

U.S. Pat. No. 4,884,071, issued to M. A. Howard et al., discloses an improved wellbore tool for coupling to a drill string at a threaded junction and adapted for use in a wellbore during drilling. A sensor is disposed in the wellbore tool for sensing a condition and producing a data signal corresponding to the condition. A self-contained power supply is disposed in the wellbore tool and coupled to the sensor for providing power to the sensor as required. The Hall Effect coupling transmitter means is carried by the sensor and transmits data from the Hall Effect coupling transmitter means to a Hall Effect coupling receiver carried by the drill string and disposed across the threaded junction from the wellbore tool. Data is transmitted across the threaded junction without requiring an electrical connection at the threaded junction. This device requires an electrical circuit and electrical excitation that may result in a catastrophic explosion.

U.S. Pat. No. 4,972,332, issued to B. L. Luebbering et al., discloses an apparatus for use on electronically controlled fuel injection systems. It senses speed, angular position, and direction of rotation using a single Hall effect type sensor. A disk element is fixedly connected to and rotatable with the camshaft of an internal combustion engine. The disk element includes a plurality of circumferential zones of substantially identical length with each zone having first and second areas. A first portion of these circumferential zones has first and second areas which are substantially different in length than the first and second areas of a second portion of the circumferential zones. Accordingly, the sensor delivers a signal which has a frequency directly related to the instantaneous velocity of the disk element, but that varies in pulse width in response to the first and second portions of the circumferential zones. A microprocessor operating under software control detects the instantaneous angular position and direction of rotation of the disk element by locating the second portion of the circumferential zones and the order in which they are received. The U.S. Pat. No. 4,972,332 apparatus measures speed and position of the rotating system as a whole and doesn't assume individual blade health.

U.S. Pat. No. 5,304,926, issued to M. T. Wu, discloses a position sensor having two magnetically sensitive devices associated with a magnet. The sensor is disposable proximate a rotatable member having at least one discontinuity in its surface. The two magnetically sensitive devices, such as Hall effect transducers, each provide output signals that represent the direction and magnitude of the magnetic field in which its respective transducer is disposed. An algebraic sum of the first and second output signals from the magnetically sensitive devices is provided as an indication of the location of the rotatable member that is disposed proximate the sensor. This device is positioned within the interior of the turbo machinery and is therefore intrusive and undesirable.

U.S. Pat. No. 5,552,711, issued to T. Deegan et al., discloses a method for determining when combustion cans or turbine blades are failing in gas turbine engines. It measures the specific ions emitted by hot spots of can and blade material when they have failed or are failing. The invention relies on the electromagnetic energy radiated by ions that are created as combustion gas erodes and ionizes the materials in these hot spots. Acceleration by the earth magnetic field and by acoustic and mechanical forces normally present in combustion machinery cause these charged particles to radiate identifiable electromagnetic emissions. The frequency of the radiation, being a function of the charge and mass of the particles, allows free ions in the exhaust stream to be identified. The device operates by measuring the electromagnetic spectrum and relating detected frequencies to the mass of the ions from can liner and blade materials. This detects the erosion of turbine/turbomachinery elements and does not detect fatigue or fracture of an element of the turbopump.

U.S. Pat. No. 6,247,900 B1, issued to C. A. Archibald et al., discloses an accurate and low cost sensing apparatus for a swash or wobble plate compressor that provides a repeatable measure of compressor speed and stroke. The apparatus includes a sensor module and a stroke sensing circuit. The compressor has an outer housing formed of aluminum or other non-magnetic material, as is customary in automotive air conditioning systems. The sensor module includes a magnetic field responsive sensor such as a Hall Effect or magnetoresistive (MR) sensor, and is attached to the periphery of the housing in proximity to a reciprocating ferrous element such as a bushing shoe on the swash or wobble plate assembly. The sensor produces a quasi-sinusoidal output voltage signal having a frequency proportional to compressor speed, and the stroke sensing circuit determines the compressor stroke by band-pass filtering, amplifying, and peak detecting the signal. This apparatus cannot provide blade-by-blade health information for rotary machinery.

SUMMARY

In a broad aspect the present invention comprises a sensing system for monitoring a property of an electrically conductive moving element of turbomachinery. The sensing system includes a sensing system housing. A magnetic core is contained within the sensing system housing. A coil is positioned about at least a portion of the core. The coil is electrically connectable to a property data analysis device. A first magnet and a second magnet are positioned about the coil and positionable proximate a moving element of turbomachinery to be monitored. A primary magnetic field is generated by the first and second magnets. When the moving element enters the primary magnetic field a current is induced in the moving element, thus generating a time-variable magnetic field and commensurate voltage signal generated in the coil. The voltage signal is amplified by the magnetic core and provides an indication of a property of the moving element. The present invention may be used with a variety of turbomachinery including, for example, gas turbines, compressors, pumps, gear boxes, jet engines, rocket engines, auxiliary power plants, etc. which can run at very high speeds, in excess of 30,000 rpm or in excess of 30,000 hz.

The sensing system of the present invention provides the means to monitor the health and operation of rotary systems. The signals provide real-time measurement of each blade's and/or impeller's gap, elongation, bending, twisting, disc precession, shaft rotational speed, torque, horsepower, runout and axial travel to detect, isolate and predict catastrophic structural failures, remaining life and needed maintenance through diagnostic and prognostic algorithms. These signals can also be used to control the turbomachinery to maximize operational limits of the rotary systems, providing faster response, longer life, and more efficient thermodynamic and pumping operation. The higher thermodynamic efficiency is achieved through directly measuring the hardware degradation, rather than reducing the maximum operating temperature at a single point based on averaged gas temperature to provide a safety margin for the blades. The higher pumping efficiency is achieved by the use of tighter impeller gaps, which is possible because of precise and real-time impeller-gap measurement.

Other objects, advantages, and novel features will become apparent from the following detailed description of the invention when considered in conjunction with the accompanying drawings.

BRIEF DESCRIPTION OF THE DRAWINGS

FIG. 3b is a side view of the turbopump assembly of FIG. 3a.

FIG. 5a is a diagram showing examples of blade sensing system signal shapes.

FIG. 5b is a diagram showing examples of impeller sensing system signal shapes.

FIG. 5c is a diagram showing the shaft-end sensing system signal with calibration.

The same parts or elements throughout the drawings are designated by the same reference characters.

DETAILED DESCRIPTION OF THE INVENTION

Figure 1A:
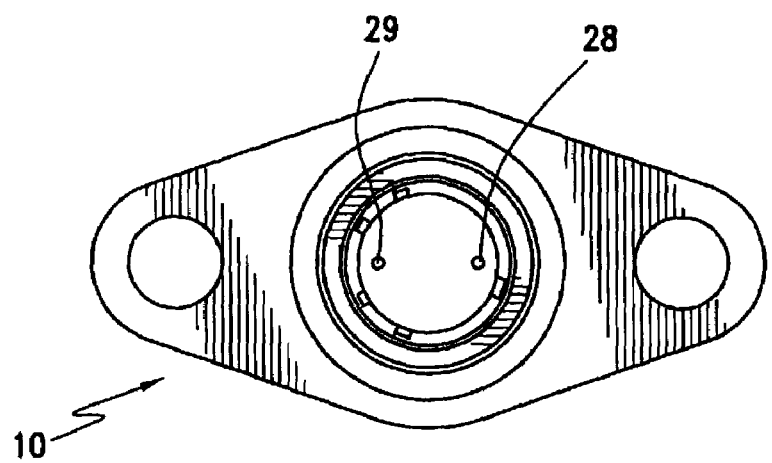
FIG. 1a is a top view of sensing system of the present invention.
Figure 1B:
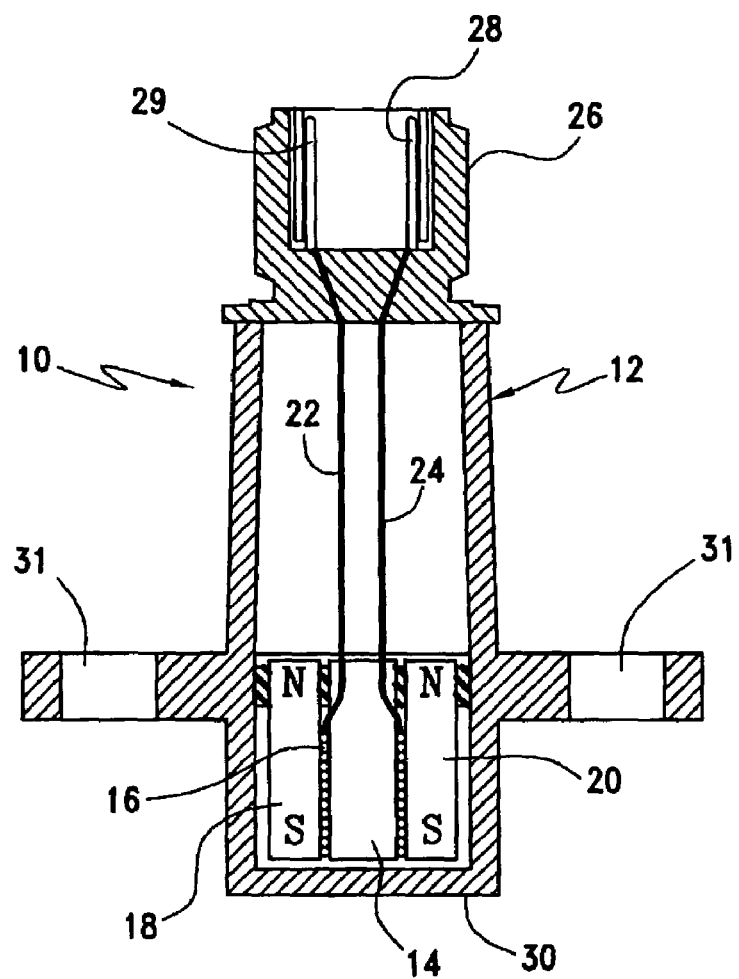
FIG. 1b is a side cross-sectional view of the sensing system of the present invention.

Referring now to the drawings and the characters of reference marked thereon, FIGS. 1a and 1b illustrate a preferred embodiment of the sensing system of the present invention, designated generally as 10. The sensing system 10 includes a sensing system housing 12 that is preferably formed of a nonmagnetic metal such as steel, stainless steel, brass, or aluminum, or a non-metallic material such as a ceramic, plastic, elastomer, composite, etc.

A magnetic core 14 is contained within the housing 12. The magnetic core 14 may be, for example, a soft iron, ferrite, etc.

A conductive coil 16 is positioned about at least a portion of the core 14. The coil 16 may have dozens of turns and may include multiple superimposed layers of copper, aluminum or other conductive insulated wires.

Magnets 18, 20 are positioned about the coil 16 and are positioned within the housing 12. The sensing system 10 is positioned so that the magnets 18, 20 are positioned proximate a moving element or a plurality of moving elements of turbomachinery to be monitored, as will be explained below in more detail. These magnets 18, 20 can be symmetric in polarity, i.e. both having their north pole facing toward the moving elements, or, asymmetric, having one magnet north pole aimed at the moving element and the other magnet having its north pole aimed away from the moving elements. In the embodiment shown in FIG. 1 the two static magnetic fields oppose and cancel each other everywhere except between the magnets, thus providing a very narrow magnetization region, which, in turn, provides a very crisp magnetic contour of the moving element. This allows detection of minute variations in the moving elements. In contrast, the asymmetric configuration provides a larger signal but more blurred contour of the moving element. The moving element may be, for example, a rotating blade, impeller, shaft, gear, or disc. Each moving element may be either magnetic or non-magnetic. Magnetic elements produce a large signal but must be conductive so that eddy currents can be generated inside it.

First and second electrically conductive leads 22, 24 are connected to the coil 16 at one end. The other ends of the leads 22, 24 are connected thru a connector 26 to a property data analysis device which may amplify, filter, normalize and digitize the signal to improve its signal-to noise ratio. The connector 26 of the sensing system 10 contains two pins 28, 29 that provide connectivity between the leads 22, 24 and the analysis device. The signal property being analyzed may be, for example, the position of the moving element relative to said sensing system, bending or twisting of the moving element, its electrical conductivity, magnetic permeability, temperature, axial or radial speed, axial or radial position, or blade, impeller, gear intrinsic oscillation.

Although, in FIG. 1 the magnets 18, 20 are shown radially spaced about the coil 16 and oriented symmetrically with respect to each other they may be in other suitable positions. They may, for example, be oriented asymmetrically.

During operation, the sensing system 10 is preferably positioned in a "blind hole" portion of the turbomachinery, near the moving element. This "blind hole" portion has a thin walled portion of the housing wall that is sufficiently thick to provide pressure isolation and leakage prevention. The bottom portion 30 of the sensing system 10 is the portion of the system 10 that is positioned in the housing "blind hole" portion. It may be securely positioned via openings 31 and conventional fastening elements, with bolts through the flange or by a thread of the sensing housing, not shown. When the sensing system 10 is positioned in the "blind hole" a primary magnetic field is generated by the first and second magnets. When the moving element enters the primary magnetic field a current is induced in the moving element. This, in turn, generates a time-variable magnetic field and commensurate voltage signal in the coil 16. The voltage signal is amplified by the magnetic core. The voltage signal provides an indication of a multitude of properties of the moving element.

Figure 2:
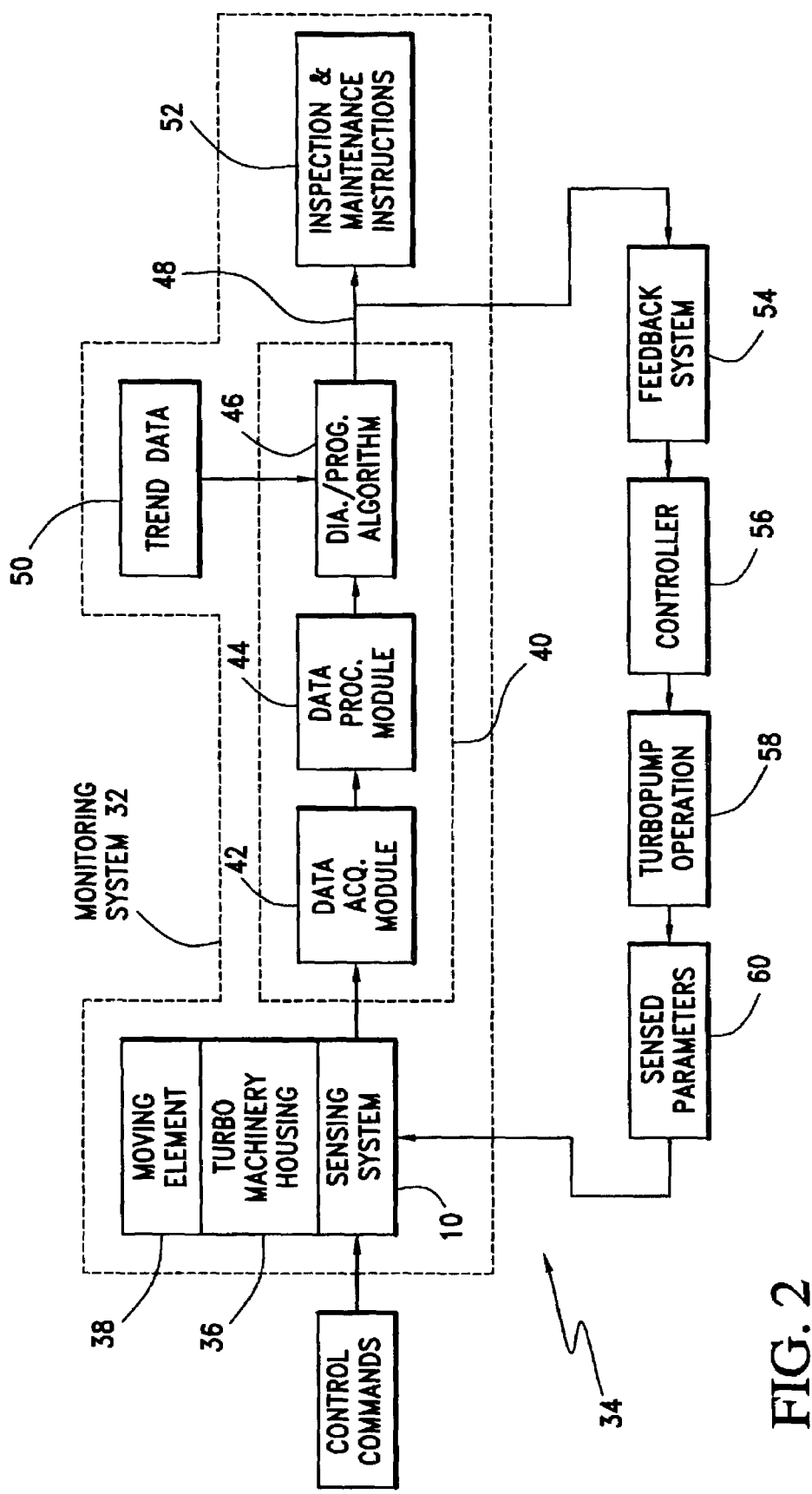
FIG. 2 is a schematic illustration of the overall control system of the present invention.

Referring now to FIG. 2, integration of the sensing system 10 into a monitoring system, designated generally as 32, and into an overall control system, designated generally as 34, is illustrated. The monitoring system 32 includes a turbomachinery housing 36 including at least one thin walled portion and a moving element 38. The electrically conductive moving element 38 is contained within the turbomachinery housing 36 proximate a thin walled portion of the housing 36. The thin walled portion of the housing 36 must be sufficiently close to moving element 38 such that the generated signal in the coil is larger than the noise in the coil to allow detectability. In situations where a non-intrusive sensing system is not required, the turbomachinery housing may contain an opening for insertion of the sensing system.

A data analysis system 40 of the monitoring system 32 includes a data acquisition module 42 for acquiring the voltage signal. The data acquisition module 42 may comprise, for example, electronic circuitry capable of optimally interfacing with the coil electrical impedance and producing a maximum signal-to-noise and broad frequency response. A data processing module 44 renders the acquired voltage signal compatible with a desired display or recording system. The data processing module 44 provides a processed signal. The data processing module 44 may comprise, for example, commercially available electronic filters, amplifiers, normalizers, digitizers, etc. An algorithm module 46 converts the processed signal to provide indications of the health status 48 of the moving element based on trend data 50. The health status 48 might include the spent fatigue life of each element as well as the remaining life, thus identifying the failing component and predicting its life and needed maintenance. The algorithm module 46 includes comparing algorithms for receiving the processed signals from the data processing module 44 and comparing the processed signals with a trend relationship for providing diagnostic and prognostic information. Diagnostic and prognostic algorithms receive the diagnostic and prognostic information and provide logistics instructions, i.e. instructions for maintenance, inspection or overhaul.

The health status indications are used to provide inspection and maintenance instructions 52. This might include inspection of the moving elements for deformation, and/or erosion, as well as inspection of stationary parts, i.e. housing, nozzles, vanes, etc. The maintenance may include replacement of elements such as blades, bearings, impellers, etc. The monitoring system may provide information as to when to perform the maintenance, i.e. after how many flights and duration of operation.

A feedback system 54 receives real-time instantaneous control signals of the status of the moving elements from the algorithm module 46 and provides a plurality of feedback signals to a turbomachinery operating controller 56. The turbomachinery operating controller 56 receives the feedback signals and utilizes the feedback signals to adjust, in real time, the operation level (temperature, pressure, flow, speed, etc.) of the turbomachinery in accordance with the status of the moving elements to maximize the operating efficiency and capacity of the turbomachinery and hydrodynamic efficiency. This type of control system will allow operation at, for example, higher temperatures, providing more power or higher efficiency with the same hardware. This is possible because current turbomachinery does not measure blade bending, twisting, elongation. Instead only housing interior temp is measured and controlled. The maximum temperature allowable is determined with many safety margins due to lack of precise knowledge of the blade structural health. For safety reasons, the designers set the controlled temperature at a lower level, which in turn, reduces the efficiency and the power capacity. The new operating conditions affect the moving element properties through the sensing system 10 in real-time, as indicated by blocks 58, 60. The controller, based on several health indicating parameters, may command to slow down or completely shut down the turbomachinery.

Figure 3B:
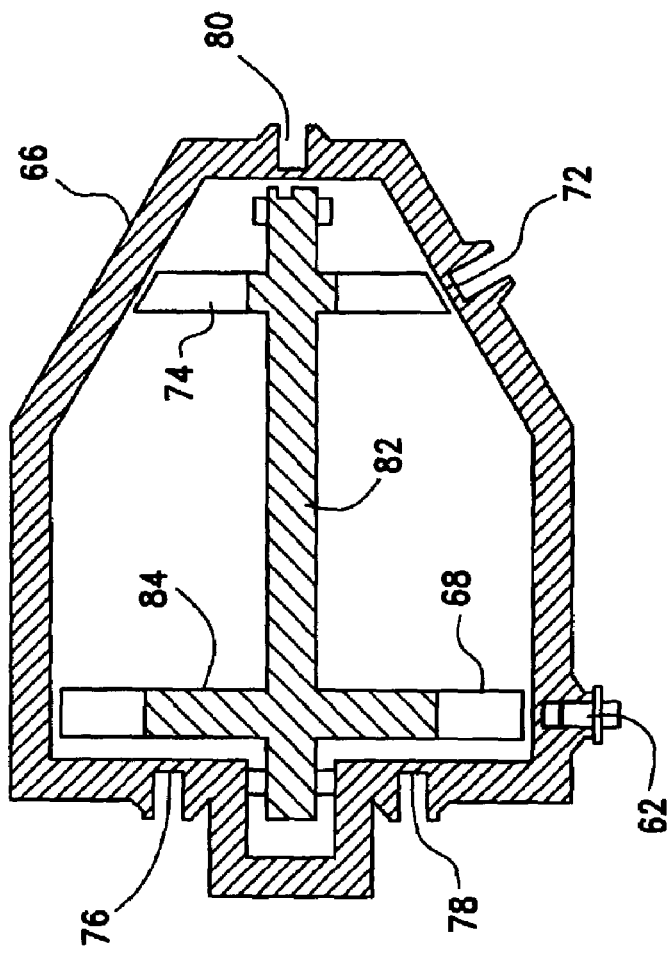
Figure 3A:
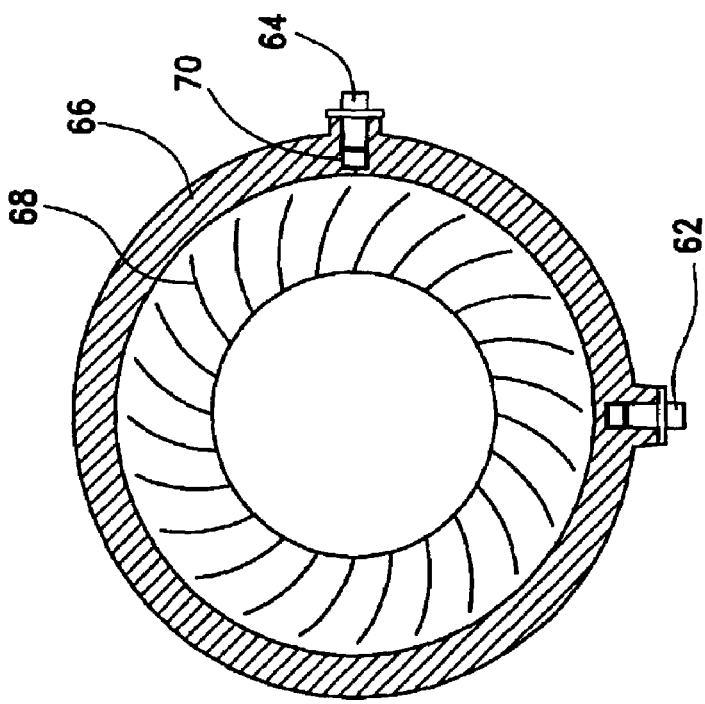
FIG. 3a is an end view showing the positioning of various sensing systems in a turbopump assembly.

Referring now to FIGS. 3a and 3b, a specific example of the integration of the sensing system in turbomachinery, i.e. a turbopump, is illustrated. Two radially positioned sensing systems 62, 64 are positioned, say, 90 degrees apart within the turbomachinery housing 66 in the vicinity of the blades 68. The sensing systems 62, 64 are facing the blades 68 for blade runout, gap, bending, twisting and travel measurements. The sensing systems 62, 64 fit within "blind holes", i.e. thin walled portions 70 of the turbomachinery housing 66. Such thin walled portions 70 should be sufficiently thick to provide pressure isolation and leakage protection. Generally, they should be thick enough to withstand the internal pressures but sufficiently thin to provide a maximum signal. They could range from say about 0.5 to 0.010 inches in conventional aerospace applications.

FIG. 3b shows a thin walled portion 72 in which a sensing system can be positioned in the vicinity of the impellers 74. Another sensing system (not shown) can be positioned approximately 90 degrees apart from thin walled portion 72 within the turbomachinery housing 66. These two sensing systems would face the impellers for impeller runout, gap, bending, twisting and travel measurements.

Two radially positioned thin walled portions (not shown, but located adjacent to sensing systems 62 or 64 in an axially offset position) face the blades for placement of sensing systems for measuring blade twisting. A thin walled portion 80 at the end of the shaft 82 can be used to position a sensing system for measuring shaft axial travel. Axially positioned thin walled portions 76, 78 face the disc 84 for measuring disc precession. As can be seen, this judicious use of positioning arrangements allows for the monitoring of multiple turbopump parameters.

Figure 4:
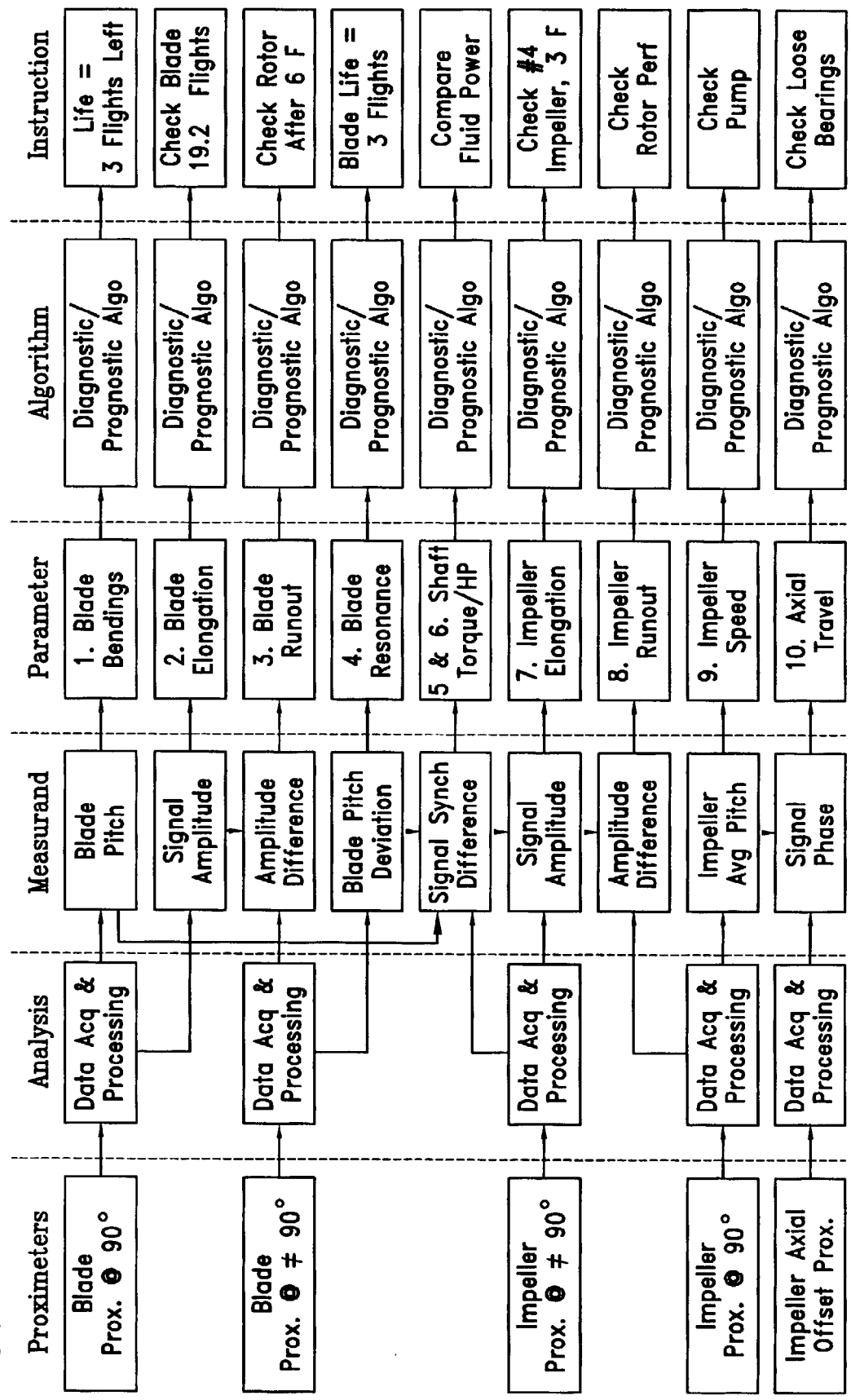
FIG. 4 illustrates the algorithm module of the monitoring system of the present invention.

FIG. 4 illustrates the various signal processing algorithms that may be utilized:

a) The signal amplitude of a radially oriented sensing system positioned in the plane of the disc provides elongation of each blade.

b) The signal amplitude of a radially oriented sensing system positioned in the plane of the impeller provides elongation of each impeller.

c) The signal pitch, transit time between two adjacent blades, of a radially oriented sensing system positioned in the plane of the disc provides the bending of each blade.

d) The signal pitch, transit time between two adjacent blades, of a radially oriented sensing system positioned in the plane of the impeller provides the bending of each impeller.

e) The signal pitches, transit time between two adjacent blades, of multiple radially oriented sensing systems positioned in the plane of the disc and circumferentially odd multiples of excitation wavelength quarters provide the resonant oscillation amplitude of each blade (not shown in the figure).

f) The combined signal amplitudes of two of the radially oriented sensing systems positioned in the plane of the disc and circumferentially apart from each other provides run out of the shaft at the disc plane.

g) The combined signal amplitudes of two radially oriented sensing systems positioned in the plane of the impeller and circumferentially apart from each other provides run out of the shaft at the impeller plane.

h) The average signal pitch, transit time between two adjacent blades, of a radially oriented sensing system positioned in the plane of the impeller provides the shaft rotary speed.

i) The difference of averaged position of blade and impeller radially oriented sensing systems provides the shaft torque/twist.

j) The product of shaft torque and shaft speed provides the power of the shaft (not shown in the figure).

k) The difference of two axially oriented sensing systems positioned against the disc provides the wobble/precession of the disc.

l) The difference of two axially oriented sensing systems positioned against the shaft end provides the shaft axial travel.

FIG. 5a illustrates an example of signals derived from a blade sensing system. As can be seen by reference to this figure the normal blades have signals 86 with almost equal spacings and amplitudes. Shaft run out is indicated by signals 88 of greater amplitude. Elongated blades have signals 90 with even greater amplitudes. Rubbing blades have very high amplitude signals 92. Blade bending is indicated by an uneven transit-time between blades signals. Blade twisting is indicated by the difference of the transit times between axially offset sensing systems. Speed is indicated by the average spacings between the blade transit times.

FIG. 5b illustrates an example of signals derived from an impeller sensing system. As can be seen run out (94), rubbing (96), and elongation (98) can be detected. Furthermore, a comparison of the blade and impeller reference signals can be used to determine torque.

FIG. 5c illustrates the amplitude difference between signals 100, 102 of yet another set of sensors. These sensors are located perpendicular to the disc and measure disc precession or wobbling.

The present invention has numerous novel features. It provides direct rotary-system real-time hardware-degradation monitoring and controlling techniques. It is non-intrusive (although not required to be so, depending on the desired application). It may be manufactured to include a one-piece housing. It is passive. It may operate in a very high speed environment, exceeding 20,000 hz.

Among it, numerous benefits include the following: no leaks; no interference with flow; no parasitic pressure drop; not affected by the flow; no electrical power need (i.e. simple electronics); no electrical excitation in hazardous media (i.e. safe); provides real-time life prediction; real-time rubbing (i.e. could cause explosion) prediction; real-time fault detection; real-time fault isolation (blade-by-blade or impeller-by-impeller); real-time fault prediction; same technology or even the same sensor for monitoring of blades, impellers, shaft, gear and disc.

The present invention is applicable for use with a wide variety of high speed machinery such as rocket engine technology; auxiliary-power and jet engines; helicopter gearbox; and, engines.

Perhaps the most important advantage of the present invention is that it provides for more efficient and more powerful turbines with the same hardware design and more efficient pumps with tighter gaps than heretofore possible, still providing safe operation.

Obviously, many modifications and variations of the present invention are possible in light of the above teachings. It is, therefore, to be understood that within the scope of the appended claims, the invention may be practiced otherwise than as specifically described.

The invention claimed is:

1. A sensing system for monitoring a property of an electrically conductive moving element of turbomachinery, comprising:
   a) a sensing system housing;
   b) a magnetic core contained within said sensing system housing;
   c) a coil positioned about at least a portion of said core, said coil being electrically connectable to a property data analysis device; and,
   d) a first magnet and a second magnet oriented symmetrically with respect to the first magnet, each of said magnets being positioned about said coil and being positionable proximate a moving element of turbomachinery to be monitored, wherein a primary magnetic field is generated by said first and second magnets, wherein when said moving element enters said primary magnetic field a current is induced in said moving element, thus generating a time-variable magnetic field and commensurate voltage signal generated in said coil, said voltage signal being amplified by said magnetic core, said voltage signal providing an indication of a property of said moving element.

2. The sensing system of claim 1, wherein said property comprises the position of said moving element relative to said sensing system.

3. The sensing system of claim 1, wherein said property comprises the bending of said moving element.

4. The sensing system of claim 1, wherein said property comprises the twisting of said moving element.

5. The sensing system of claim 1, wherein said property comprises the electrical conductivity of said moving element.

6. The sensing system of claim 1, wherein said property comprises the magnetic permeability of said moving element.

7. The sensing system of claim 1, wherein said property comprises the temperature of said moving element.

8. The sensing system of claim 1, wherein said property comprises the speed of said moving element.

9. The sensing system of claim 1, wherein said property comprises the axial speed of said moving element.

10. The sensing system of claim 1, wherein said property comprises the axial position of said moving element.

11. The sensing system of claim 1, wherein said property comprises the radial speed of said moving element.

12. The sensing system of claim 1, wherein said property comprises the radial position of said moving element.

13. The sensing system of claim 1, wherein said property comprises the blade, impeller, or gear oscillation of said moving element.

14. The sensing system of claim 1, wherein said moving element is magnetic.

15. The sensing system of claim 1, wherein said first and second magnets are radially spaced about said coil.

16. The sensing system of claim 1, wherein said coil is electrically connectable to the property data analysis device via a first electrically conductive lead and a second electrically conductive lead.

17. A monitoring system for turbomachinery, comprising:
 a) a turbomachinery housing for containing at least one electrically conductive moving element; and,
 b) a sensing system positioned proximate said moving element for monitoring a property of said electrically conductive moving element, said sensing system, comprising:
  i) a sensing system housing;
  ii) a magnetic core contained within said sensing system housing;
  iii) a coil positioned about at least a portion of said core, said coil being electrically connectable to a property data analysis device; and,
  iv) a first magnet and a second magnet, each of said magnets being positioned about said coil and being positionable proximate a moving element of turbomachinery to be monitored, a primary magnetic field being generated by said first and second magnets, wherein when said moving element enters said primary magnetic field a current is induced in said moving element, thus generating a time-variable magnetic field and commensurate voltage signal generated in said coil, said voltage signal being amplified by said magnetic core, said voltage signal providing an indication of a property of said moving element; and
 c) a data analysis system, comprising:
  a data acquisition module for acquiring said voltage signal;
  a data processing module for rendering said acquired voltage signal compatible with a desired display, said data processing module providing a processed signal; and,
  an algorithm module for converting said processed signal to provide indications of the health status of said moving element.

18. The monitoring system of claim 17, wherein said turbomachinery housing includes at least one thin walled portion, said sensing system being positioned at said thin walled portion.

19. The monitoring system of claim 17, wherein said turbomachinery housing includes an opening to accommodate said sensing system.

20. The monitoring system of claim 17, wherein said turbomachinery housing is formed of non-electrically conductive material.

21. The monitoring system of claim 17, wherein said at least one moving element comprises a plurality of moving elements said monitoring system further including a data analysis system, comprising:
 a) a data acquisition module for acquiring said voltage signal;
 b) a data processing module for rendering said acquired voltage signal compatible with a desired display, said data processing module providing processed signals; and,
 c) an algorithm module for converting said processed signals to provide indications of the status of said plurality of moving elements, said algorithm module, comprising:
  i) a plurality of comparing algorithms for receiving said processed signals and comparing said processed signals with a trend relationship for providing diagnostic and prognostic information; and,
  ii) a plurality of diagnostic and prognostic algorithms for receiving said diagnostic and prognostic information and providing logistics instructions.

22. The monitoring system of claim 17, wherein said thin walled portion is sufficiently thick to provide pressure isolation.

23. The monitoring system of claim 17, wherein said thin walled portion is sufficiently thick to provide leakage prevention.

24. The monitoring system of claim 17, wherein said thin walled portion is formed of non-conductive material on the order of 1.0 to 0.010 inches thick.

25. A control system for controlling a property of at least one of a plurality of electrically conductive moving elements of turbomachinery, comprising:
 a) a monitoring system for turbomachinery, comprising:
  i) a sensing system positioned proximate said at least one of said plurality of electrically conductive moving elements, said sensing system providing an indication of a property of said moving element; and,
  ii) a data analysis system for acquiring said indication, providing a processed signal therefrom, and converting said processed signal to provide indications of the status of said moving element, said data analysis system including an algorithm module for providing real-time control signals;
 b) a feedback system for receiving said real-time control signals from said algorithm module and providing a plurality of feedback signals; and,
 c) a turbomachinery operating controller for receiving said feedback signals and utilizing said feedback signals to adjust the operation level of said turbomachinery in accordance with said status of said plurality of moving elements to maximize the operating efficiency of said turbomachinery.

26. The control system of claim 25, wherein said algorithm module further provides inspection and maintenance instructions.

27. The control system of claim 25, wherein said turbomachinery comprises a turbine and said optimization comprises maximizing the thermodynamic efficiency.

28. The control system of claim 25, wherein said turbomachinery comprises a turbine and said optimization comprises minimizing blade fracture risk.

29. The control system of claim 25, wherein said turbomachinery comprises a pump mid said optimization comprises maximizing the hydrodynamic efficiency.

30. The control system of claim 25, wherein said turbomachinery comprises a gear box and said optimization comprises maximizing the life of the gear box.

31. The control system of claim 25, wherein said turbomachinery comprises a pump and said optimization comprises minimizing rubbing failures.

32. The control system of claim 25, wherein the status of each of said plurality of moving elements are monitored separately from the remaining other moving elements.

33. The control system of claim 25, wherein said turbomachinery operating controller adjusts the operation level of said turbomachinery in accordance with the position of said moving element.

34. The control system of claim 25, wherein said turbomachinery operating controller adjusts the operation level of said turbomachinery in accordance with the bending of said moving element.

35. The control system of claim 25, wherein said turbomachinery operating controller adjusts the operation level of said turbomachinery in accordance with the twisting of said moving element.

36. The control system of claim 25, wherein said turbomachinery operating controller adjusts the operation level of said turbomachinery in accordance with the electrical conductivity of said moving element.

37. The control system of claim 25, wherein said turbomachinery operating controller adjusts the operation level of said turbomachinery in accordance with the magnetic permeability of said moving element.

38. The control system of claim 25, wherein said turbomachinery operating controller adjusts the operation level of said turbomachinery in accordance with the temperature of said moving element.

39. The control system of claim 25, wherein said turbomachinery operating controller adjusts the operation level of said turbomachinery in accordance with the speed of said moving element.

40. The control system of claim 25, wherein said turbomachinery operating controller adjusts the operation level of said turbomachinery in accordance with the axial position of said moving element.

41. The control system of claim 25, wherein said turbomachinery operating controller adjusts the operation level of said turbomachinery in accordance with the blade oscillation of said moving element.

42. A method for controlling a property of at least one of a plurality of electrically conductive moving elements of turbomachinery, comprising the steps of:
   a) monitoring selected turbomachinery, comprising the steps of:
      i) providing an indication of a property of the moving element by utilizing a sensing system positioned proximate said at least one of said plurality of electrically conductive moving elements; and,
      ii) acquiring said indication, providing a processed signal therefrom and converting said processed signal to provide indications of the status of the moving element, via a data analysis system, said data analysis system including an algorithm module for providing real-time control signals;
   b) receiving said real-time control signals from said algorithm module and providing a plurality of feedback signals, via a feedback system; and,
   c) receiving said feedback signals and utilizing said feedback signals to adjust the operation level of said turbomachinery in accordance with said status of said plurality of moving elements to maximize the operating efficiency of said turbomachinery.

43. A monitoring system for turbomachinery, comprising:
   a turbomachinery housing for containing a plurality of electrically conductive moving elements; and,
   a sensing system positioned proximate said moving element for monitoring a property of said electrically conductive moving elements, said sensing system, comprising:
      a sensing system housing;
      a magnetic core contained within said sensing system housing;
      a coil positioned about at least a portion of said core, said coil being electrically connectable to a property data analysis device; and,
      a first magnet and a second magnet, each of said magnets being positioned about said coil and being positionable proximate a moving element of turbomachinery to be monitored, a primary magnetic field being generated by said first and second magnets, wherein when said moving elements enter said primary magnetic field a current is induced in said moving elements, thus generating a time-variable magnetic field and commensurate voltage signal generated in said coil, said voltage signal being amplified by said magnetic core, said voltage signal providing an indication of a property of said moving elements; and
   a data analysis system, comprising:
      a data acquisition module for acquiring said voltage signal;
      a data processing module for rendering said acquired voltage signal compatible with a desired display, said data processing module providing processed signals; and,
      an algorithm module for converting said processed signals to provide indications of the status of said plurality of moving elements, said algorithm module, comprising:
         a plurality of comparing algorithms for receiving said processed signals and comparing said processed signals with a trend relationship for providing diagnostic and prognostic information; and,
         a plurality of diagnostic and prognostic algorithms for receiving said diagnostic and prognostic information and providing logistics instructions.

44. The monitoring system of claim 43, wherein the first magnet and the second magnet are oriented symmetrically with respect each other, and wherein the first and second magnets define a gap there between in which the primary magnetic field is generated by said first and second magnets.

* * * * *

UNITED STATES PATENT AND TRADEMARK OFFICE
CERTIFICATE OF CORRECTION

PATENT NO.       : 7,392,713 B2                                     Page 1 of 1
APPLICATION NO.  : 10/260315
DATED            : July 1, 2008
INVENTOR(S)      : Barkhoudarian It is certified that error appears in the above-identified patent and that said Letters Patent is hereby corrected as shown below:

Claim 29, Column 10, line 54: "mid" should read as --and--

Signed and Sealed this

Twentieth Day of January, 2009

JON W. DUDAS
*Director of the United States Patent and Trademark Office*